United States Patent
Giovanetti et al.

(10) Patent No.: US 7,989,658 B2
(45) Date of Patent: Aug. 2, 2011

(54) PROCESS FOR THE PURIFICATION OF GABAPENTIN

(75) Inventors: Roberto Giovanetti, Schio (IT); Andrea Nicoli, Vicenza (IT); Livius Cotarca, Friuli (IT)

(73) Assignee: ZaCh System S.p.A., Bresso (IT)

( * ) Notice: Subject to any disclaimer, the term of this patent is extended or adjusted under 35 U.S.C. 154(b) by 1079 days.

(21) Appl. No.: 11/722,056

(22) PCT Filed: Dec. 15, 2005

(86) PCT No.: PCT/EP2005/056817
§ 371 (c)(1), (2), (4) Date: Jun. 18, 2007

(87) PCT Pub. No.: WO2006/064041
PCT Pub. Date: Jun. 22, 2006

(65) Prior Publication Data
US 2009/0292138 A1    Nov. 26, 2009

(30) Foreign Application Priority Data

Dec. 17, 2004    (IT) .............................. MI2004A2418

(51) Int. Cl.
C07C 227/40    (2006.01)
C07C 229/28    (2006.01)

(52) U.S. Cl. ....................................................... 562/507
(58) Field of Classification Search ........................ None
See application file for complete search history.

(56) References Cited

U.S. PATENT DOCUMENTS

| | | |
|---|---|---|
| 6,518,456 B1 | 2/2003 | Peverali et al. |
| 2004/0063997 A1 | 4/2004 | Ferrari et al. |
| 2004/0068011 A1 | 4/2004 | Cannata et al. |
| 2007/0123590 A1 | 5/2007 | Giovanetti et al. |
| 2007/0129569 A1 | 6/2007 | Cotarca et al. |

FOREIGN PATENT DOCUMENTS

| | | |
|---|---|---|
| WO | 2004 093779 | 11/2004 |

*Primary Examiner* — Daniel Sullivan
*Assistant Examiner* — Yevegeny Valenrod
(74) *Attorney, Agent, or Firm* — Oblon, Spivak, McClelland, Maier & Neustadt, L.L.P.

(57) ABSTRACT

The present invention relates to a process for the purification of gabapentin. The process relates to the addition of hydrochloric acid to an aqueous solution or suspension of gabapentin, before, during or after the concentration step of that solution, and the subsequent slurry of the gabapentin by the addition of an alcoholic solvent. The so obtained gabapentin has an high purity degree and, in particular, is characterized by a low content of lactam.

25 Claims, No Drawings

PROCESS FOR THE PURIFICATION OF GABAPENTIN

CROSS-REFERENCE TO RELATED APPLICATIONS

This application is a 371 of PCT/EP2005/056817 filed Dec. 15, 2005 and claims the benefit of Italy MI2004A002418 filed Dec. 17, 2004.

The present invention relates to a process for the purification of gabapentin. Gabapentin, namely 1-aminomethyl-1-cyclohexanacetic acid of formula

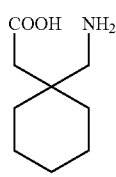

(I)

is a drug widely used in therapy.

The drug has been described for the first time in U.S. Pat. No. 4,024,175 and, afterwards, several processes for its preparation have been disclosed in the patent literature.

The main problem addressed by the known processes for the preparation of gabapentin is the purity of the compound, in particular the need to avoid the presence of a by-product, namely 2-aza-spiro[4.5]decan-2-one of formula

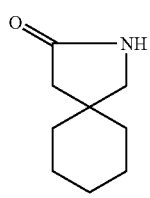

(II)

also known as gabapentin lactam, in view of its toxicity.

In fact, according to the U.S. Pharmacopoeia, the amount of gabapentin lactam in the active ingredient gabapentin must be lower than 0.05%.

Another important purity requirement for gabapentin is the chloride content which must be not more than 0.01% (i.e. not more than 100 ppm).

For an almost exhaustive reference to the known processes for the preparation of gabapentin see the following patent documents: U.S. Pat. No. 4,024,175; WO 00/58268; WO 02/034709; EP 1 475 366; U.S. Pat. No. 4,152,326; U.S. Pat. No. 4,960,931; U.S. Pat. No. 5,068,413; U.S. Pat. No. 5,132,451; U.S. Pat. No. 6,054,482; WO 99/14184; WO 99/18063; WO 03/031391; U.S. Pat. No. 4,956,473; U.S. Pat. No. 5,095,148; WO 98/28255; WO 00/64857; WO 00/39074; WO 02/044123; WO 2004/031126; WO 02/074727; U.S. Pat. No. 6,521,788; U.S. Pat. No. 6,518,456; WO 03/062185; WO 03/070683; WO 2004/101489; WO 03/089403; WO 2004/046084; WO 2004/046085; WO 2004/046108; US 2004/0176639; EP 1468985; WO 2004/093779; WO 2004/093780 and any counterpart thereof.

As it can be seen from the above listed prior art literature, in most of the processes for the preparation of gabapentin, a gabapentin salt, generally the gabapentin hydrochloride, is the last synthetic intermediate. This salt is in most cases subjected to ion exchange treatment or to neutralization with a suitable base or acid for the conversion to gabapentin.

According to other processes, gabapentin is obtained directly from a precursor by reduction, hydrolysis or similar reactions.

Gabapentin is finally isolated in solid crystalline form from a solution or suspension of pure gabapentin. Especially when an ion exchange resin is used, the work-up of an aqueous solution of pure gabapentin is required to isolate gabapentin in solid crystalline form.

However, in most of the known processes, this work-up comprises a long evaporation of water under reduced pressure and gentle heating (25-45° C.).

Even under these mild conditions, the prolonged heating of a gabapentin solution inevitably results with the formation of the undesired lactam with the consequent decrease of overall yields and the need of an additional purification of solid gabapentin to keep the lactam content below the required limit of 0.05%.

We have now found that the formation of lactam during the usual work-up of gabapentin solutions can be remarkably lower by adding hydrochloric acid.

Therefore, object of the present invention is a process for isolating pure gabapentin from an aqueous solution or suspension of gabapentin which comprises:

(a) providing an aqueous solution or suspension of gabapentin, (b) concentrating the gabapentin solution or suspension up to obtain a slurry, and (c) isolating pure gabapentin from the slurry, characterized in that a diluted or concentrated solution of hydrochloric acid in an amount, expressed as hydrochloric acid, ranging from 3 g to 20 g for 1000 g of gabapentin is added before, during or after the concentration of the gabapentin solution or suspension of step (a).

Gabapentin obtained with the process object of the present invention is pure stable gabapentin with a lactam content lower than 0.05% and a chloride content not more than 0.01% (100 ppm), according to the Pharmacopoeia requirements.

In a preferred embodiment, the process of the present invention is particularly suitable for the preparation of pure stable gabapentin containing more than 20 ppm of chloride from hydrochloric acid.

In another preferred embodiment, the process object of the present invention is particularly suitable for the preparation of pure stable gabapentin containing more than 20 ppm of chloride from hydrochloric acid starting from a solution of gabapentin containing a carboxylic acid alkaline salt.

The aqueous solution or suspension of step (a) according to the present invention is a solution of essentially pure gabapentin in a solvent mixture containing water, preferably a solution of gabapentin in water.

When the aqueous solution or suspension of step (a) of the present process contains one or more additional solvents, the additional solvent or solvents are usually an organic solvent miscible with water, preferably an alcoholic solvent or a mixture of alcoholic solvents.

Preferred alcoholic solvents are methanol, ethanol, n-propanol, isopropanol, n-butanol, isobutanol, sec-butanol, t-butanol and mixture thereof.

Methanol, ethanol, isopropanol and mixture thereof are the most preferred, a mixture of methanol and isopropanol being still more preferred.

The aqueous solution of step (a) can also contain some amounts of a base depending on the process for the preparation of gabapentin it comes from. Usually the base can be ammonia or an amine, especially a secondary o tertiary amine, or a carboxylic acid alkaline salt. In this case the amount of hydrochloric acid to add, according the process object of the present invention, will be higher due to the neutralising effect of the base.

Moreover, depending on the used synthetic process for the preparation of gabapentin, the aqueous solution or suspension of step (a) of the present process can contain some amounts of salts which can eventually have a neutralizing effect to be calculated when the addition of hydrochloric acid is carried out.

The man skilled in the art can easily evaluate the eventual effect of any salts present in the gabapentin solution/suspension of step (a) according to the present process and adjust the amount of hydrochloric acid accordingly.

In a preferred embodiment, the aqueous solution of step (a) of the present process is an aqueous solution coming from the elution of an ion exchange resin.

In a most preferred embodiment, the aqueous solution comes from the elution through a strong cationic exchange resin and can contain some ammonia.

The concentration according to step (b) of the present process can be carried out before, during or after the addition of hydrochloric acid.

The concentration is carried out according to known methods, generally by gentle heating at a maximum temperature of 40-45° C. and under reduced pressure.

The length of the concentration step mainly depends on the amount of water in the aqueous solution or suspension of gabapentin and on the heating temperature.

Also the subsequent isolation of pure gabapentin is carried out according to known methods. The man skilled in the art will appreciate that any conventional isolation method can be used for step (c) of the present invention.

In a practical embodiment of the process object of the present invention, the isolation is carried out by filtration or centrifugation of the solid gabapentin obtained after treatment of the slurry from step (b) with an alcoholic solvent or with a mixture of alcoholic solvents.

Preferred alcoholic solvents are methanol, ethanol, n-propanol, isopropanol, n-butanol, isobutanol, sec-butanol, t-butanol and mixture thereof.

Methanol, ethanol, isopropanol and mixture thereof are the most preferred, a mixture of methanol and isopropanol being still more preferred.

The filtered or centrifuged gabapentin from step (c) of the present process is washed according to usual methods.

Preferably one or more washings with small volumes of the same alcoholic solvents used for the treatment of the slurry according to step (c) above are carried out, before drying the solid gabapentin.

In a preferred embodiment of the process object of the present invention the final washing is carried out with a mixture of methanol and isopropanol, eventually in the presence of an electrolyte. A preferred electrolyte in the washing mixture is sodium chloride.

The characterising step of the process object of the present invention is the addition of hydrochloric acid.

This addition can be carried out at any step of the whole purification process and this versatility is one of the advantageous features of the process.

As already underlined, the addition of hydrochloric acid can be made before, during or after the concentration step (b). Preferably this addition is carried out at the last phase of the concentration step (b).

The added hydrochloric acid can be used as a diluted or concentrated aqueous solution, but a concentrated aqueous solution is preferred to minimize the amount of additional water.

For practical reasons, a 31% w/w concentrated aqueous hydrochloric solution is most preferably used in the process object of the present invention.

The amount of hydrochloric acid will range from 3 g to 20 g for each 1000 g of gabapentin and will depend also from the eventual presence of bases in the solution/suspension/slurry containing gabapentin which hydrochloric acid is added to.

In the presence of some amounts of a base it will be necessary to add an increased amount of hydrochloric acid, generally from 9 g to 20 g/1000 g of gabapentin.

In the absence of bases in the solution/suspension/slurry containing gabapentin, an amount of hydrochloric acid falling within a narrower range, generally from 3 g to 15 g/1000 g of gabapentin, will be suitable.

In a particularly preferred embodiment of the process object of the present invention, a concentrated aqueous hydrochloric acid solution is added to a slurry of gabapentin in methanol, isopropanol and water.

The addition of hydrochloric acid during the work-up for the isolation of pure gabapentin, according to the present invention, allows to reduce the formation of toxic gabapentin lactam usually occurring during the work-up.

Therefore, this addition of hydrochloric acid represents a simple solution to a well-known and difficult-to-solve problem related to the manufacturing of gabapentin.

The simplicity of the addition of hydrochloric acid together with its versatility, which makes it suitable for practically any known process for the preparation of gabapentin, is at the same time the most advantageous and the most unexpected feature of the present invention.

It is worth noting, in this respect, that most of the industrial processes for the preparation of gabapentin provides for the preparation of a gabapentin acid addition salt, generally the gabapentin hydrochloride salt, followed by its conversion to gabapentin.

It is evident to the man skilled in the art that, after the addition of hydrochloric acid according to the process object of the present invention, some hydrochloric gabapentin salt will be formed.

For this reason, the process object of the present invention is particularly suitable for the preparation of gabapentin containing more than 20 ppm of chloride from hydrochloric acid.

However, pure gabapentin containing less than 20 ppm of chloride from hydrochloric acid can be prepared with the process object of the present invention as well.

A practical preferred embodiment of the process object of the present invention is the following.

An aqueous gabapentin solution containing ammonia is obtained by elution through a strong cationic exchange resin.

This aqueous solution is heated at a temperature of 40-45° C. under reduced pressure.

During the first phase of the heating ammonia evolves and the concentration is continued under the same conditions up to obtaining a slurry.

After treatment of the slurry with a mixture of methanol and isopropanol, an aqueous concentrated hydrochloric acid solution is added and gabapentin is separated by centrifugation. After washings with a mixture of methanol, isopropanol and sodium chloride, the resultant pure gabapentin is dried in oven at a temperature not more than 45° C.

The resultant gabapentin has a content of lactam lower than 0.05% and a chloride content not more than 0.01%, according to Pharmacopoeia requirements.

To better illustrate the present invention without limiting it, the following examples are now given.

EXAMPLE 1

To an ammonia solution containing gabapentin, 2.56 g of hydrochloric acid at 31% (p/p) and the solution thereby obtained was concentrated in a vacuum at no more than 45° C. When 90% of water was distilled, 47 g of methanol are added, the suspension thus obtained was heated to 50-55° C. for 0.5 hours and 196 g of isopropanol were added. Heating was continued at 50-55° C. for 1 hour, the suspension was chilled to −5° C. and, after 2 hours, the solid was filtered, washed with isopropanol and then with a mixture of isopropanol/water/sodium chloride. The product was then dried obtaining 67 g of gabapentin having a total impurity content of 0.09% (w/w) and 30-80 ppm of chloride anions.

EXAMPLE 2

The eluate containing gabapentin was concentrated in a vacuum at no more than 45° C. When 90% of the water had been distilled, 162 g of methanol and 7.4 g of hydrochloric acid at 31% (w/w) were added. The suspension thus obtained was heated to 50-55° C. for 0.5 hours and 679 g of isopropanol were added. Heating was continued at 50-55° C. for 1 hour, the suspension was chilled to −5° C. and maintained at this temperature for 1 hour. The solid was filtered, washed with isopropanol and then with a mixture of isopropanol/water/sodium chloride. The product was then dried obtaining 223 g of gabapentin (85% yield).

EXAMPLE 3

The eluate containing gabapentin was concentrated in a vacuum at no more than 35° C. When 90% of the water had been distilled, 260 kg of methanol were added. The suspension thus obtained was heated to 50-55° C. for 1 hour, then 1080 kg of isopropanol and 12.5 kg of hydrochloric acid at 31% (w/w) were added. After 1 hour at 50-55° C., the suspension was chilled to −5° C. and maintained at this temperature for 1 hour. The solid was filtered, washed with 22 kg of isopropanol and then with a total quantity of 185 kg of mixture of isopropanol/water/sodium chloride. The product was dried obtaining 355 kg of gabapentin (84% yield) having 35-40 ppm of chlorides.

EXAMPLE 4

The eluate containing gabapentin was concentrated in a vacuum at no more than 35° C. When 90% of the water had been distilled, 260 kg of methanol were added. The suspension thus obtained was heated to 50-55° C. for 1 hour, then 1080 kg of isopropanol were added. After 1 hour at 50-55° C. for 1 hour, the solution was cooled to 20° C. and 12.5 kg of hydrochloric acid at 31% (w/w) were added. The mixture was chilled to −5° C. and maintained at this temperature for 1 hour. The solid was filtered, washed with 22 kg of isopropanol and then with a total quantity of 185 kg of mixture of isopropanol/water/sodium chloride. The product was dried obtaining 360 kg of gabapentin (85% yield) having 35-40 ppm of chlorides.

The invention claimed is:

1. A process for isolating pure gabapentin from a solution or from a suspension of gabapentin, which comprises:
    (a) providing an aqueous solution or suspension of gabapentin,
    (b) concentrating the gabapentin solution or suspension up to obtain a slurry, and
    (c) isolating pure gabapentin from the slurry,
wherein a diluted or concentrated solution of hydrochloric acid in an amount, expressed as hydrochloric acid, ranging from 3 g to 20 g for 1000 g of gabapentin is added to the aqueous solution or suspension of gabapentin before, during or after the concentration of the gabapentin solution or suspension of step (a); wherein the aqueous solution or suspension of gabapentin in step (a) is an aqueous solution coming from the elution of an ionic exchange resin.

2. The process according to claim 1 for the preparation of pure stable gabapentin containing more than 20 ppm of chlorides from hydrochloric acid.

3. The process according to claim 1 for the preparation of pure stable gabapentin containing more than 20 ppm of chlorides from hydrochloric acid starting from a gabapentin solution containing an alkaline salt of a carboxylic acid.

4. The process according to claim 1, wherein the solution or suspension of the step (a) is a solution of essentially pure gabapentin in a solvent mixture containing water.

5. The process according to claim 4, wherein the aqueous solution is a solution of gabapentin in water.

6. The process according to claim 4, wherein the solution or suspension of the step (a) contains one or more organic solvents miscible with water.

7. The process according to claim 6, wherein the organic solvent miscible with water is an alcoholic solvent or a mixture of alcoholic solvents.

8. The process according to claim 7, wherein the alcoholic solvents are methanol, ethanol, n-propanol, isopropanol, n-butanol, isobutanol, sec-butanol, t-butanol and mixtures thereof.

9. The process according to claim 8, wherein the solvent is methanol, ethanol, isopropanol and mixtures thereof.

10. The process according to claim 9, wherein the solvent is a mixture of methanol and isopropanol.

11. The process according to claim 1, wherein the aqueous solution or suspension of the step (a) contains a base.

12. The process according to claim 11, wherein the base is ammonia or a secondary or tertiary amine, or an alkaline salt of a carboxylic acid.

13. The process according to claim 1, wherein the aqueous solution or suspension of the step (a) contains salts.

14. The process according to claim 1, wherein the aqueous solution comes from the elution through a strong cationic exchange resin and contains ammonia.

15. The process according to claim 1, wherein the isolation is carried out by filtration or centrifuging of the solid gabapentin obtained after treating the slurry from the step (b) with an alcoholic solvent or with a mixture of alcoholic solvents.

16. The process according to claim 15, wherein the alcoholic solvent or mixture of alcoholic solvents are methanol, ethanol, n-propanol, isopropanol, n-butanol, isobutanol, sec-butanol, t-butanol or mixtures thereof.

17. The process according to claim 16, wherein the alcoholic solvent is methanol, ethanol, isopropanol or mixtures thereof.

18. The process according to claim 17, wherein the solvent is a mixture of methanol and isopropanol.

19. The process according to claim 1, wherein the addition of hydrochloric acid is carried out before the concentration step (b).

20. The process according to claim 1, wherein the addition of hydrochloric acid is carried out during the concentration step (b).

21. The process according to claim 1, wherein the addition of hydrochloric acid is carried out after the concentration step (b).

22. The process according to claim 1, wherein the hydrochloric acid is added as a concentrated aqueous solution.

23. The process according to claim 22, wherein the hydrochloric acid is a concentrated aqueous solution at 31% w/w.

24. The process according to claim 1, wherein the quantity of hydrochloric acid is between 9 g and 20 g for each 1000 g of gabapentin.

25. The process according to claim 1, wherein the quantity of hydrochloric acid is between 3 g and 15 g for each 1000 g of gabapentin.

* * * * *